(12) United States Patent
Nakahara et al.

(10) Patent No.: US 8,519,013 B2
(45) Date of Patent: Aug. 27, 2013

(54) METHOD FOR PRODUCING FORMIC ACID

(75) Inventors: Masaru Nakahara, Shiga (JP);
Nobuyuki Matsubayashi, Kyoto (JP);
Yoshiro Yasaka, Kyoto (JP)

(73) Assignee: Masaru Nakahara, Shiga (JP)

( * ) Notice: Subject to any disclaimer, the term of this patent is extended or adjusted under 35 U.S.C. 154(b) by 0 days.

(21) Appl. No.: 13/574,859

(22) PCT Filed: Jan. 24, 2011

(86) PCT No.: PCT/JP2011/051164
§ 371 (c)(1),
(2), (4) Date: Jul. 24, 2012

(87) PCT Pub. No.: WO2011/093229
PCT Pub. Date: Aug. 4, 2011

(65) Prior Publication Data
US 2012/0295991 A1 Nov. 22, 2012

(30) Foreign Application Priority Data
Jan. 27, 2010 (JP) .................................. 2010-015249

(51) Int. Cl.
*C07C 27/00* (2006.01)

(52) U.S. Cl.
USPC ....................................................... 518/700

(58) Field of Classification Search
USPC ........................................................ 518/700
See application file for complete search history.

(56) References Cited

U.S. PATENT DOCUMENTS

| 2007/0036706 | A1 | 2/2007 | Ogo et al. | |
|---|---|---|---|---|
| 2008/0221353 | A1* | 9/2008 | Tsunashima | .................... 564/12 |
| 2011/0158899 | A1 | 6/2011 | Nakahara et al. | |

FOREIGN PATENT DOCUMENTS

| CN | 101328590 | 12/2008 |
|---|---|---|
| CN | 101337939 | 1/2009 |
| JP | 7-173098 | 7/1995 |
| JP | 07-330666 | 12/1995 |
| JP | 2001-192676 | 7/2001 |
| JP | 2005-289742 | 10/2005 |
| JP | 2009-078200 | 4/2009 |
| WO | 2005/028408 | 3/2005 |

OTHER PUBLICATIONS

U.S. Appl. No. 13/534,467, filed Jun. 27, 2012.
U.S. Appl. No. 13/645,982, filed Oct. 5, 2012.
Zhang et al., "Hydrogenation of Carbon Dioxide is Promoted by a Task-Specific Ionic Liquid", Angewandte Chemie International Edition, Dec. 18, 2007, pp. 1127-1129.
Ohlin et al., "Carbon Dioxide Reduction in Biphasic Aqueous-ionic Liquid Systems by Pressurized Hydrogen", High Pressure Research, Sep. 2003, pp. 239-242.
Zhang et al., "Hydrogenation of CO2 to Formic Acid Promoted by Diamine-Functionalized Ionic Liquid", ChemSusChem, Mar. 5, 2009, pp. 234-238.
Yasaka et al., "Controlling the Equilibrium of Formic Acid with Hydrogen and Carbon Dioxide Using Ionic Liquid", Journal of Physical Chemistry A, Feb. 18, 2010, pp. 3510-3515.
Fukuzumi et al., "Efficient Catalytic Decomposition of Formic Acid for the Selective Generation of H2 and H/D Exchange with a Water-Soluble Rhodium Complex in Aqueous Solution", ChemSusChem, vol. 1, 2008, pp. 827-834.
Urukawa et al., "Carbon Dioxide Hydrogenation Catalyzed by a Ruthenium Dihydride: A DFT and High-Pressure Spectroscopic Investigation", Chem. Eur. J., vol. 13, 2007, pp. 3886-3899.
Fellay et al., "Selective Formic Acid Decomposition for High-Pressure Hydrogen Generation: A Mechanistic Study", Chem. Eur. J., vol. 15, 2009, pp. 3752-3760.
Fellay et al., "A Viable Hydrogen-Storage System Based on Selective Formic Acid Decomposition with a Ruthenium Catalyst", Angew. Chem. Int. Ed., vol. 47, 2008, pp. 3966-3968.
Gonzalez-Calera et al., "The Selemiun-Based Hexameric Macrocycle [(Se=)P (p.-NtBu)2P(1.1.-Se)]6", Angew. Chem. Int. Ed., vol. 120, 2008, pp. 1127-1130.
Hayashi et al., "Aqueous hydrogenation of carbon dioxide catalysed by water-soluble ruthenium aqua complexes under acidic consitions", Chem. Commun, 2004, pp. 2714-2715.
Inoue et al., "Catalytic Fixation of Carbon Dioxide to Formic Acid by Transition-Metal Complexes Under Mild Conditions", Chemistry Letters, 1976, pp. 863-864.
Fukuzumi et al., "Chemsuschem", Chemhyl (10), ISSN 1864-5631, vol. 1, No. 10, 2008, pp. 789-868.
Ogo et al., "Mechanistic investigation of CO2 hydrogenation by Ru(II) and Ir(III) aqua complexes under acidic conditions: two catalytic systems differing in the nature of the rate determining step", Dalton Trans., 2006, pp. 4657-4663.
Man Ng et al., "Ruthenium-Catalyzed Hydrogenation of Carbon Dioxide to Formic Acid in Alcohols", Eur. J. Inorg. Chem., 2004, pp. 1788-1793.
Fukuzumi, "Bioinspired Energy Conversion Systems for Hydrogen Production and Storage", Eur. J. Inorg. Chem., 2008, pp. 1351-1362.
McCollum et al., "Experimental constraints on the hydrothermal reactivity of organic acids and acid anions: I. Formic acid and formate", Geochimica et Cosmochimica Acta, vol. 67, No. 19 , 2003, pp. 3625-3644.
Tsai et al., "Rhodium-Catalyzed Hydrogenation of Carbon Dioxide to Formic Acid", J. Am. Chem. Soc., vol. 114, 1992, pp. 5117-5124.
Jessop et al., "Homogeneous Catalysis in Supercritical Fluids: Hydrogenation of Supercritical Carbon Dioxide to Formic Acid, Alkyl Formates, and Formamides", J. Am. Chem. Soc., vol. 118, 1996, pp. 344-355.
Fukuzumi et al., "Unusually Large Tunneling Effect on Highly Efficient Generation of Hydrogen and Hydrogen Isotopes in pH-Selective Decomposition of Formic Acid Catalyzed by a Heterodinuclear Iridium-Ruthenium Complex in Water", J. Am. Chem. Soc., vol. 132, 2010, pp. 1496-1497.
Jessop et al., "Homogeneous catalytic hydrogenation of supercritical carbon dioxide", Nature, vol. 368, Mar. 17, 1994, pp. 231-233.

(Continued)

*Primary Examiner* — Jafar Parsa
(74) *Attorney, Agent, or Firm* — Greenblum & Bernstein, P.L.C.

(57) ABSTRACT

An object of the present invention is providing a method for producing formic acid under mild reaction conditions and by a simple procedure. As a means for achieving the object, the method for producing formic acid of the present invention is characterized by a reaction between carbon dioxide and hydrogen in the presence of an ionic liquid. According to the present invention, it is possible to generate formic acid effectively, because the method does not require that carbon dioxide be brought into a supercritical state and because no basic substances are required to be added to the reaction system.

4 Claims, 2 Drawing Sheets

(56) References Cited

OTHER PUBLICATIONS

Hull et al., "Reversible hydrogen storage using CO2 and a proton-switchable iridium catalyst in aqueous media under mild temperatures and pressures", Nature Chemistry, 18, DOI:10.1038/NCHEM.1295, Mar. 18, 2012, pp. 1-6.

Yin et al., "Promoting Effect of Water in Ruthenium-Catalyzed Hydrogenetion of Carbon Dioxide to Formic Acid", Organometallics, 20, 2001, pp. 1216-1222.

Olah et al., "Effective and Mild Ionic Hydrogenation of Corbon Monoxide, Carbon Dioxide, methyl Alcohol, Formic Acid, Carbonyl Sulfide and Carbon Disulfide to Methane with Sodium Borohydride/Trifluorome thanesulfonic(triflic)Acid", Letters, Oct. 1990, pp. 599-600.

Search report from International Application No. PCT/JP2011/051164, mail date is Apr. 5, 2011.

* cited by examiner (a) Before reaction (b) After reaction

METHOD FOR PRODUCING FORMIC ACID

TECHNICAL FIELD

The present invention relates to a method for producing formic acid.

BACKGROUND ART

Formic acid has long been playing an important role as a material for synthesis of various chemical substances such as pharmaceutical products and agricultural pesticides. Besides, as proposed by the present inventors by means of Patent Document 1, formic acid is important also as a material for production of hydrogen. There are known various methods for producing formic acid, including a method for producing formic acid from carbon dioxide and hydrogen (Patent Document 2, for example). However, Patent Document 2 proposes the reaction of carbon dioxide in a supercritical state (critical point: pressure of 73.3 bar, temperature of 31° C.) with hydrogen in the presence of a metal catalyst (group VIII transition metal complex) and an excess amount of basic substance, and therefore the method disclosed therein has following limitations: The method requires that the production facility have high pressure resistance and requires a separation process for the basic substance from the formic acid produced.

RELATED ART DOCUMENTS

Patent Documents

Patent Document 1: Japanese Unexamined Patent Application Publication No. 2005-289742
Patent Document 2: Japanese Unexamined Patent Application Publication No. HEI 7 (1995)-173098

SUMMARY OF THE INVENTION

Problems to be Solved by the Invention

The purpose of the present invention is to provide a method for producing formic acid under mild reaction conditions in a simple manner.

Means for Solving the Problems

In view of the above-described circumstances, the present inventors have made intensive studies to find that formic acid can be synthesized from carbon dioxide and hydrogen by reacting them in the presence of an ionic liquid without relying upon the supercritical state of carbon dioxide nor without adding bases to the reaction system.

The method for producing formic acid of the present invention, which has been achieved based on the above-described finding, is characterized by the presence of an ionic liquid for the reaction between carbon dioxide and hydrogen as described by claim 1.

Effects of the Invention

The present invention can provide a method for producing formic acid under mild reaction conditions and by a simple procedure, because the method does not require that carbon dioxide be brought into a supercritical state and because no basic substances are required to be added to the reaction system.

MODE FOR CARRYING OUT THE INVENTION

Figure 1:
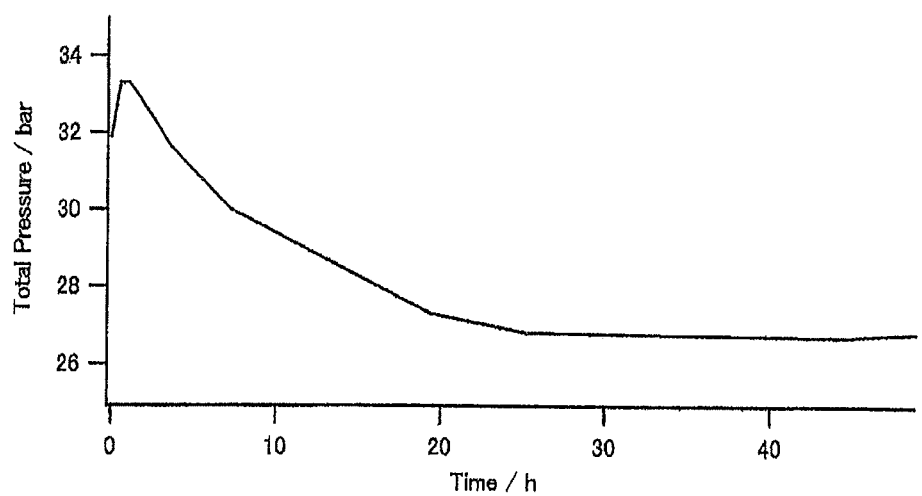
FIG. 1 is a graph showing the temporal change of the pressure in a reaction vessel in Example 1.

The method invented here for producing formic acid is characterized by the presence of an ionic liquid for the reaction between carbon dioxide and hydrogen.

In the present invention, the ionic liquid is defined as an organic compound salt having a melting point of 100° C. or less. The examples are the pyridinium-, pyrrolidinium-, and tetraalkylammonium-based ionic liquids as well as the imidazolium-based one represented by the following general formula (1) and phosphonium-based one represented by the following general formula (2).

[Formula 1]

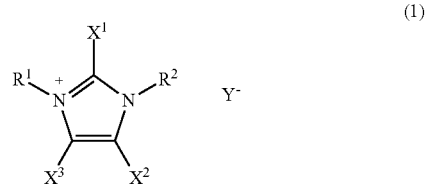

(1)

Here $R^1$ and $R^2$, the same or different, each represent an alkyl or aryl group in which one or more hydrogens may be fluorinated. $X^1$, $X^2$, and $X^3$, the same or different, each represent a hydrogen atom, a fluorine atom, or an aryl or aryl group in which one or more hydrogens may be fluorinated. The symbol $Y^-$ represents a counter-anion to the imidazolium cation.

[Formula 2]

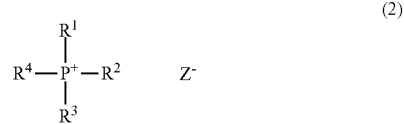

(2)

Here $R^1$, $R^2$, $R^3$, and $R^4$, the same or different, each represent an alkyl or aryl group in which one or more hydrogens may be fluorinated, and $Z^-$ represents a counter-anion to the phosphonium cation.

As the alkyl group represented by $R^1$, $R^2$, $R^3$, $R^4$, $X^1$, $X^2$, and $X^3$ in which at least one hydrogen atom may be substituted with a fluorine atom in the imidazolium-salt-based ionic liquid represented by the general formula (1) and the phosphonium-salt-based ionic liquid represented by the general formula (2), may be mentioned linear or branched alkyl and perfluoroalkyl groups each having 1 to 18 carbon atoms. Specific examples thereof include methyl, ethyl, n-propyl, iso-propyl, n-butyl, iso-butyl, sec-butyl, tert-butyl, n-pentyl, iso-pentyl, n-octyl, n-decyl, n-dodecyl, n-tetradecyl, n-octadecyl, trifluoromethyl, pentafluoroethyl, heptafluoro-n-propyl, heptafluoro-iso-propyl and nonafluoro-n-butyl groups. Examples of the aryl group in which at least one hydrogen atom may be substituted with a fluorine atom include phenyl and pentafluorophenyl groups. Examples of the counter-anion for an imidazolium cation represented by $Y^-$ and the counter-anion for a phosphonium cation represented by $Z^-$ include methanesulfonate anion ($CH_3SO_3^-$), trifluoromethanesulfonate anion ($CF_3SO_3^-$), bis(trifluoromethanesulfonyl)imide anion (($CF_3SO_2)_2N^-$) and formate anion ($HCO_2^-$) as well as halide ions such as chloride ion ($Cl^-$), bromide ion ($Br^-$) and iodide ion ($I^-$).

Preferred examples of the ionic liquid include an ionic liquid in which a counter-anion is a formate anion (i.e., formic acid salt), which is, as a medium for the production of formic acid by using carbon dioxide and hydrogen as raw materials, excellent in reaction selectivity (high-purity formic acid is produced) and reaction velocity. The ionic liquid in which a counter-anion is a formate anion can be synthesized, for example, from an ionic liquid in which a counter-anion is different from a formate anion such as bromide ion, by an anion exchange method with the use of a strong-basic ion exchange resin (Biomacromolecules, Vol. 7, 3295-3297, 2006). Various kinds of ionic liquids in which a counter-anion is different from a formate anion are commercially available. If not commercially available, such ionic liquids can be synthesized, for example, in accordance with the method described in Ionic Liquids in Synthesis I, Wiley-VCH, 2007.

For the reaction between carbon dioxide and hydrogen in the presence of an ionic liquid, for example, dry ice, which is easily handled as a carbon dioxide source is put into a pressure-resistant container containing an ionic liquid, and hydrogen is introduced thereto at a pressure of 5 bar to 50 bar, and then the ionic liquid in a liquid state is stirred. The amount of the dry ice to put in may be determined so as to give a pressure of 1 bar to 50 bar when the dry ice vaporizes. The reaction temperature is not particularly limited as long as the temperature allows the ionic liquid to stay in the liquid state. Preferably, the temperature is raised to 50° C. or more in order to produce formic acid efficiently. In this case, the upper limit of the reaction temperature is preferably 200° C., more preferably 150° C., and still more preferably 100° C., because a too high temperature may cause degradation of the ionic liquid and reduce the amount of formic acid to be produced for a thermodynamic reason. The reaction time is 1 hour to 300 hours, for example. In order to ensure a sufficient reaction velocity and prevent a side reaction, it is preferable that a metal catalyst is present in the reaction system; for example, a metal catalyst is dissolved in the ionic liquid. Examples of the metal catalyst include simple salts (chlorides, oxides, and the like) and complexes (specific examples of ligands: amines, phosphines, conjugated dienes, and the like) of transition metals (Ru, Rh, Ir, and the like) belonging to groups 8, 9 and 10 (group VIII) in the periodic table. The amount of the metal catalyst to use may be, for example, approximately 0.01 to 3% (w/w) of the amount of the ionic liquid. The method invented here requires no catalyst, whereas the method disclosed in Patent Document 2 requires the presence of a basic substance in the reaction system.

Formic acid produced through the reaction between carbon dioxide and hydrogen is accumulated in the ionic liquid. The formic acid produced can be purified easily by distillation taking advantage of an extremely low vapor pressure of the ionic liquid.

EXAMPLES

Hereinafter, the present invention will be described in detail by means of examples; however, the present invention should not be construed as being limited to the following description. Prior to experiments, the six kinds of ionic liquids shown in Table 1 were prepared.

TABLE 1

| | Kind of ionic liquid[1] | | | | | | | | |
|---|---|---|---|---|---|---|---|---|---|
| No. | $R^1$ | $R^2$ | $R^3$ | $R^4$ | $X^1$ | $X^2$ | $X^3$ | $Y^-$ | $Z^-$ |
| 1 | Me | n-Bu | — | — | H | H | H | $HCOO^-$ | — |
| 2 | Me | n-Bu | — | — | Me | H | H | $HCOO^-$ | — |
| 3 | n-Pr | n-Pr | — | — | Me | H | H | $Br^-$ | — |
| 4 | n-Pr | n-Pr | — | — | Me | H | H | $HCOO^-$ | — |
| 5 | n-Pr | n-Pr | — | — | Et | H | H | $HCOO^-$ | — |
| 6 | $n-C_6H_{13}$ | $n-C_6H_{13}$ | $n-C_6H_{13}$ | $n-C_{14}H_{29}$ | — | — | — | — | $HCOO^-$ |

[1]Each symbol corresponds to a substituent in the general formula (1) and the general formula (2). The formic acid salt ($Y^-$, $Z^-$ = $HCOO^-$) was prepared by anion exchange from a commercially available ionic liquid in which a counter-anion is different from a formate anion or an ionic liquid synthesized in accordance with the method described in Ionic Liquids in Synthesis I, Wiley-VCH, 2007. Each ionic liquid has a melting point of 100° C. or less (60° C. or less except for No. 3 ionic liquid).

Example 1

Figure 2:
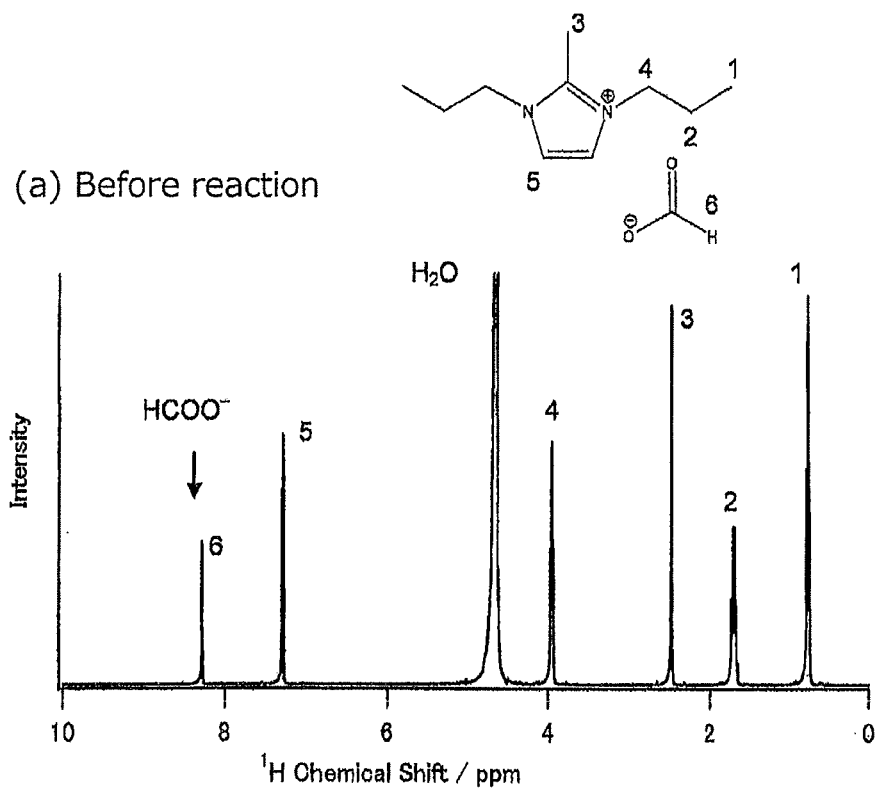
FIG. 2 is a chart of $^1$H-NMR as evidence for the formation of formic acid in the ionic liquid.
Figure 2:
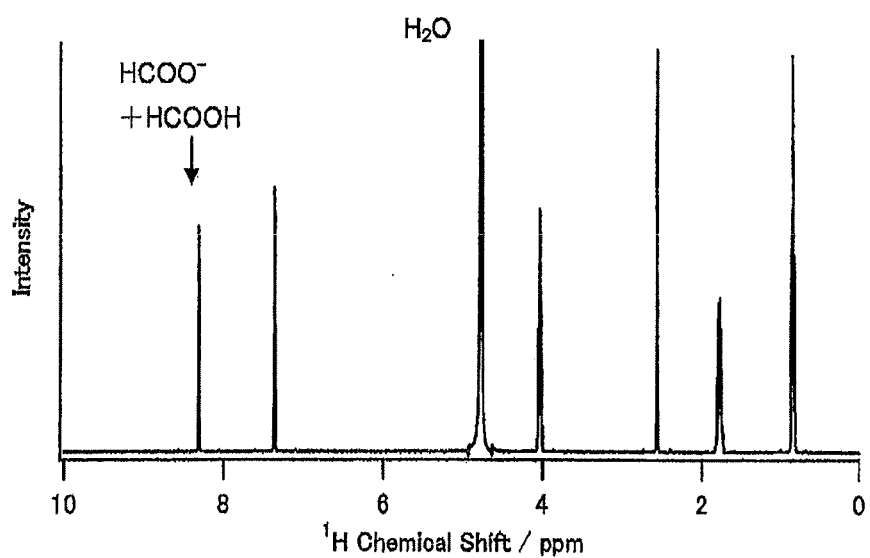

To an SUS316 reaction vessel including a Teflon® container (volume of the container: 9 mL, 25 mL including the volume of piping when connected to a manometer), a magnetic stirrer and 0.98 g of 1,3-di-n-propyl-2-methylimidazolium formate (water content: 1.5% by weight) as No. 4 ionic liquid in Table 1 in which 0.2% by weight of dichlorotetrakis (triphenylphosphine)ruthenium as a metal catalyst is dissolved were put in. To the reaction vessel cooled entirely with dry ice, 0.50 g of dry ice was put in. The manometer and a hydrogen bottle were connected to the reaction vessel to introduce hydrogen thereto at a pressure of 20.0 bar, while vaporization of the dry ice therein was being prevented. The reaction vessel was made hermetic by closing a connection valve, and then the temperature was returned to normal temperature (room temperature). As a result, the dry ice vaporized and the pressure in the reaction vessel changed to 31.9 bar (carbon dioxide pressure: 10.9 bar; air pressure: 1 bar). The reaction vessel was placed in an oil bath at 60° C., and the magnetic stirrer was rotated to monitor the pressure in the reaction vessel. The pressure in the reaction vessel increased to 33.3 bar in the first 30 minutes, and then gradually decreased due to generation of formic acid through the reaction between carbon dioxide and hydrogen to be constant at 26.8 bar after 30 hours (FIG. 1). After 49 hours, the reaction vessel was opened to find that the sample changed to a flowable liquid through the reaction, while the sample before the reaction was a viscous liquid that crystallizes at 20° C. The metal catalyst was deactivated by adding water to the sample, and then $^1$H-NMR analysis was performed to determine the quantity of formic acid produced in the sample. FIG. 2 shows the result. As obvious from FIG. 2, comparison between the results before the reaction (a) and after the reaction (b) has revealed that the signal intensity of the formic acid around 8 ppm increased, and formic acid in a concentration of 2.48 mol/L (amount of substance: 2.5 mmol) was produced in the sample.

Examples 2 to 5

Carbon dioxide and hydrogen were reacted under the same conditions as in Example 1 except that the amount of the dry ice put in and the pressure for the hydrogen introduced were changed. Table 2 shows the results. It is clear in Table 2 that formic acid can be formed depending on the amount of the dry ice placed and pressures for the hydrogen introduced.

TABLE 2

| Ex. No. | $H_2$ partial pressure before reaction (bar)*[1] | $CO_2$ partial pressure before reaction (bar)*[2] | Reaction time (h) | Concentration of formic acid produced (mol/L) | Amount of formic acid produced (mmol) |
| --- | --- | --- | --- | --- | --- |
| 2 | 19.0 | 15.2 | 96 | 2.60 | 2.6 |
| 3 | 20.0 | 7.2 | 75 | 2.33 | 2.3 |
| 4 | 10.2 | 12.1 | 160 | 1.44 | 1.4 |
| 5 | 5.2 | 12.0 | 116 | 0.2*[3] | 0.2*[4] |

*[1]Corresponding to the pressure for the $H_2$ introduction under cooling with dry ice.
*[2]Values measured at room temperature; the total pressure = pressure for $H_2$ introduced + air pressure.
*[3]Determination precision, ±0.1 mol/L.
*[4]Determination precision, ±0.1 mmol.

Example 6

Using No. 1 ionic liquid instead of No. 4 in Table 1 with the other reaction conditions kept the same as those in Example 1, it has been confirmed that formic acid is generated by the reaction between carbon dioxide and hydrogen.

Example 7

Using No. 2 ionic liquid instead of No. 4 in Table 1 with the other reaction conditions kept the same as those in Example 1, it has been confirmed that formic acid is generated by the reaction between carbon dioxide and hydrogen.

Example 8

Using No. 3 ionic liquid instead of No. 4 in Table 1 with the other reaction conditions kept the same as those in Example 1, it has been confirmed that formic acid is generated by the reaction between carbon dioxide and hydrogen.

Example 9

Using No. 5 ionic liquid instead of No. 4 in Table 1 with the other reaction conditions kept the same as those in Example 1, it has been confirmed that formic acid is generated by the reaction between carbon dioxide and hydrogen.

Example 10

Using No. 6 ionic liquid instead of No. 4 in Table 1 with the other reaction conditions kept the same as those in Example 1, it has been confirmed that formic acid is generated by the reaction between carbon dioxide and hydrogen.

Example 11

Without using metal catalysts and with all of the other reaction conditions kept the same as those in Example 1, it has been confirmed that formic acid is generated by the reaction between carbon dioxide and hydrogen.

Example 12

Using No. 1 ionic liquid instead of No. 4 in Table 1 without metal catalysts and with all of the other reaction conditions kept the same as those in Example 1, it has been confirmed that formic acid is generated by the reaction between carbon dioxide and hydrogen.

Example 13

Using No. 2 ionic liquid instead of No. 4 in Table 1 without metal catalysts and with all of the other reaction conditions kept the same as those in Example 1, it has been confirmed that formic acid is generated by the reaction between carbon dioxide and hydrogen.

Example 14

Using No. 3 ionic liquid instead of No. 4 in Table 1 without metal catalysts and with all of the other reaction conditions kept the same as those in Example 1, it has been confirmed that formic acid is generated by the reaction between carbon dioxide and hydrogen.

Example 15

Using No. 5 ionic liquid instead of No. 4 in Table 1 without metal catalysts and with all of the other reaction conditions kept the same as those in Example 1, it has been confirmed that formic acid is generated by the reaction between carbon dioxide and hydrogen.

Example 16

Using No. 6 ionic liquid instead of No. 4 in Table 1 without metal catalysts and with all of the other reaction conditions kept the same as those in Example 1, it has been confirmed that formic acid is generated by the reaction between carbon dioxide and hydrogen.

Reference Example 1

Another method for synthesis of 1,3-di-n-propyl-2-methylimidazolium formate (No. 4 ionic liquid in Table 1)

2-Methylimidazole was reacted with 1 equivalent of sodium hydride in 1,2-dimethoxyethane as a solvent at room temperature, and then 3 equivalents of 1-bromopropane was gradually added thereto, followed by stirring at 60° C. for 2 days. Approximately 1 day after start of stirring, an appropriate amount of 2-propanol was added thereto as a co-solvent. After completion of stirring, the solvent and unreacted 1-bromopropane were distilled off. The residual solid was recrystallized with acetone twice to obtain 1,3-di-n-propyl-2-methylimidazolium bromide as transparent and colorless crystals (No. 3 ionic liquid in Table 1). Next, the 1,3-di-n-propyl-2-methylimidazolium bromide was dissolved in water, and 1 equivalent of silver sulfate was added thereto, followed by stirring at room temperature for approximately 1 hour. The precipitate of resulting silver bromide was removed by filtration, and then water was distilled off. The residual solid was recrystallized with acetonitrile to obtain 1,3-di-n-propyl-2-methylimidazolium sulfate as white fine crystals. Subsequently, the 1,3-di-n-propyl-2-methylimidazolium sulfate was dissolved in water at 80° C., 1 equivalent of barium formate was added thereto, and the precipitate of resulting barium sulfate was removed by filtration. Water was removed from the aqueous solution of 1,3-di-n-propyl-2-methylimidazolium formate obtained as described above at 60° C. under reduced pressure to obtain desired 1,3-di-n-propyl-2-methylimidazolium formate as a colorless and highly viscous liquid.

Reference Example 2

Another method for synthesis of tri-n-hexyl-n-tetradecylphosphonium formate (No. 6 ionic liquid in Table 1)

Commercially available tri-n-hexyl-n-tetradecylphosphonium chloride was dissolved in methanol, and 1 equivalent of potassium formate was added thereto. The precipitate of resulting potassium chloride was removed by filtration, and then the methanol was distilled off to obtain desired tri-n-hexyl-n-tetradecylphosphonium formate as a colorless and highly viscous liquid.

INDUSTRIAL APPLICABILITY

The present invention is industrially applicable in that it can provide a method for producing formic acid under mild reaction conditions and by a simple procedure, because the method does not require that carbon dioxide be brought into a supercritical state or a basic substance be added to the reaction system.

The invention claimed is:

1. A method for producing formic acid comprising reacting carbon dioxide and hydrogen in the presence of an ionic liquid without using metal catalysts.

2. The method according to claim 1, wherein an imidazolium-salt-based ionic liquid represented by the following formula is used as an ionic liquid:

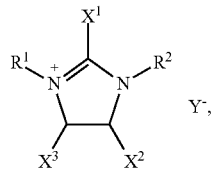

wherein $R^1$ and $R^2$ are the same or different, and represent an alkyl group with at least one hydrogen atom being optionally substituted with a fluorine atom, or an aryl group with at least one hydrogen atom being optionally substituted with a fluorine atom;

$X^1$, $X^2$, and $X^3$ are the same or different, and represent an alkyl group with at least one hydrogen atom being optionally substituted with a fluorine atom, an aryl group with at least one hydrogen atom being optionally substituted with a fluorine atom, a hydrogen atom, or a fluorine atom; and $Y^-$ represents a counteranion for an imidazolium cation.

3. The method according to claim 1, wherein a phosphonium-salt-based ionic liquid represented by the following formula is used as an ionic liquid:

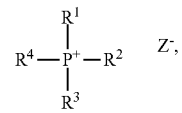

wherein $R^1$, $R^2$, $R^3$, and $R^4$ are the same or different, and represent an alkyl group with at least one hydrogen atom being optionally substituted with a fluorine atom, or an aryl group with at least one hydrogen atom being optionally substituted with a fluorine atom; and $Z^-$ represents a counteranion for a phosphonium cation.

4. The method according to claim 1, wherein an ionic liquid in which a counteranion is a formate anion is used as an ionic liquid.

* * * * *